United States Patent [19]
Kelly et al.

[11] Patent Number: 5,407,419
[45] Date of Patent: * Apr. 18, 1995

[54] ENCLOSURE WITH INTEGRAL TIE MEMBER

[75] Inventors: Joseph L. Kelly, Charlestown, Va.; Robert S. Jenkins, Boston, Mass.

[73] Assignee: Kellcover, Inc., Charlestown, Mass.

[*] Notice: The portion of the term of this patent subsequent to Aug. 30, 2011 has been disclaimed.

[21] Appl. No.: 14,592

[22] Filed: Feb. 8, 1993

Related U.S. Application Data

[63] Continuation-in-part of Ser. No. 891,121, Jun. 1, 1992, Pat. No. 5,342,286.

[51] Int. Cl.⁶ .............................. A61F 13/00
[52] U.S. Cl. .......................... 602/3; 383/71; 383/77
[58] Field of Search .............. 602/3, 60-63; 128/DIG. 15; 383/62, 74, 77, 71, 210, 211

[56] References Cited

U.S. PATENT DOCUMENTS

| | | |
|---|---|---|
| 1,619,887 | 3/1927 | Sapp . |
| 2,849,171 | 8/1958 | O'Brien, Jr. . |
| 3,107,842 | 10/1963 | Guilfoyle .............................. 383/71 |
| 3,140,815 | 7/1964 | Majesky ............................... 383/77 |
| 3,186,626 | 1/1965 | Shvetz ................................. 383/77 |
| 4,036,220 | 7/1977 | Bellasaima . |
| 4,639,945 | 2/1987 | Betz . |
| 4,727,864 | 3/1988 | Wiesenthal .......................... 602/3 |
| 4,911,151 | 3/1990 | Rankin ................................ 602/3 |
| 4,966,135 | 10/1990 | Renfrew ............................. 602/3 |
| 5,046,621 | 9/1991 | Bell ................................... 206/627 |

FOREIGN PATENT DOCUMENTS

| | | | |
|---|---|---|---|
| 6916747 | 12/1970 | Netherlands ..................... | 383/71 |
| 9008071 | 7/1990 | WIPO .............................. | 383/77 |

*Primary Examiner*—Robert A. Hafer
*Assistant Examiner*—David J. Kenealy
*Attorney, Agent, or Firm*—Christopher W. Brody; Lowe, Price, LeBlanc & Becker

[57] ABSTRACT

An enclosure for covering extremities or containing material such as trash or other objects or articles is described. The enclosure is a sack-like member having a lip extending above the opening or along a side edge of the sack-like member. The lip includes a perforation extending along a portion of the length thereof, either parallel to the opening or to the side edge. An adhesive strip with a removable covering may extend along the length of the lip at selected portions thereof. In use, the perforation is torn to separate the lip into a tie member and a securing member that remains attached to the sack-like member. In one embodiment, an extremity may be inserted into the sack-like member and the tie member can be used to secure the opening around the extremity. In another embodiment, the tie member can be used to seal the opening of the sack-like member such that the enclosure can be used as a container or receptacle in a desired application. When enclosing or covering an extremity, the enclosure protects a bandage or cast portion of the extremity from water. The enclosure may be sterilized to create a sterile environment within the sack member.

12 Claims, 4 Drawing Sheets

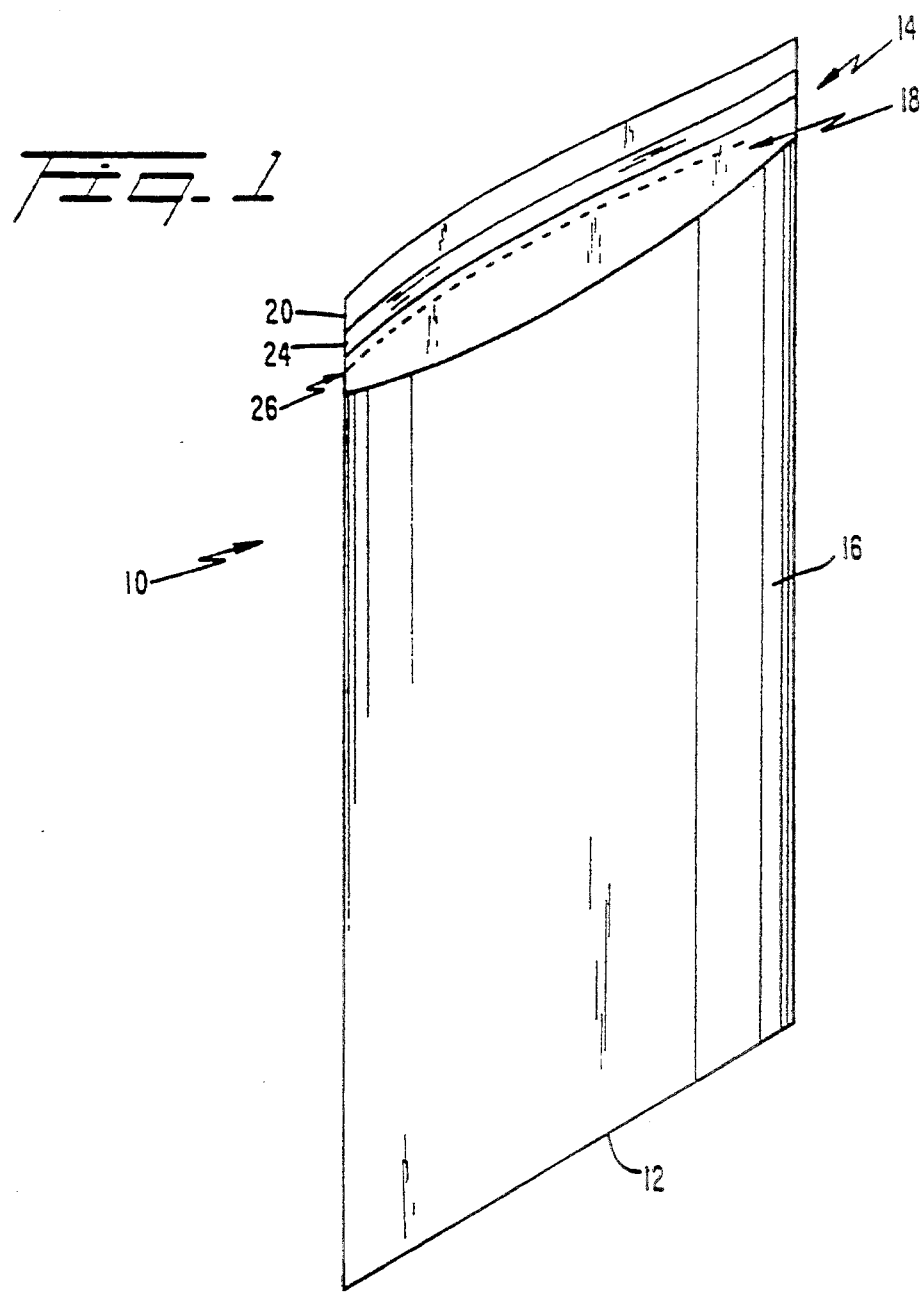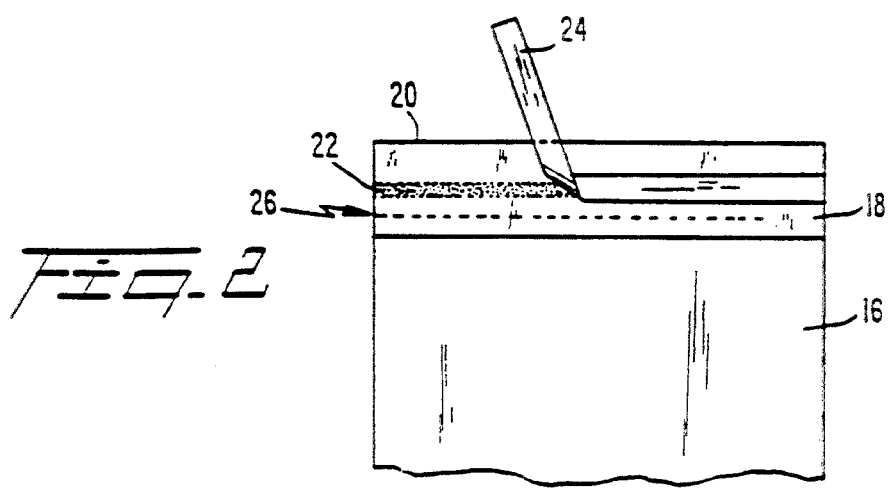

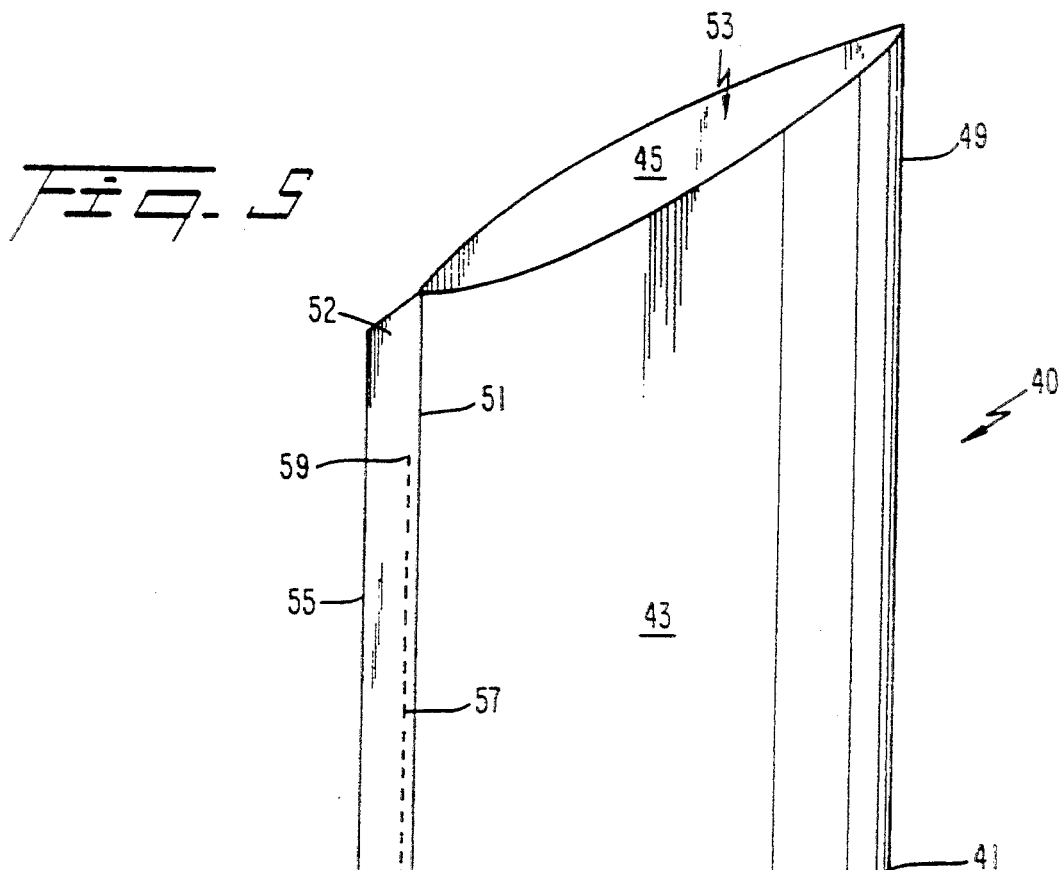
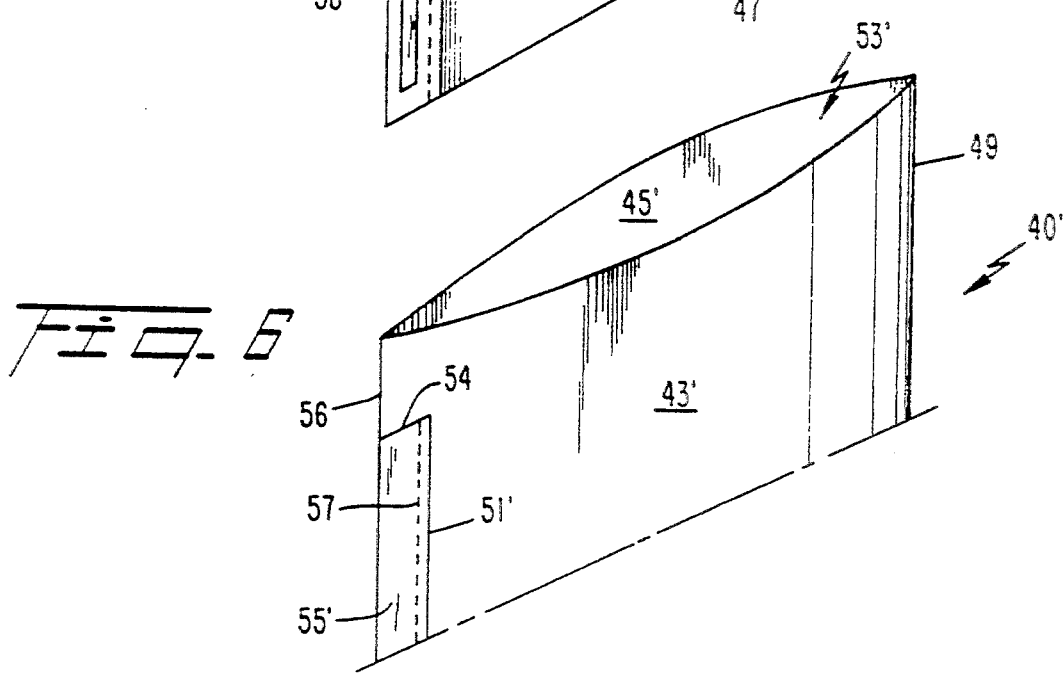

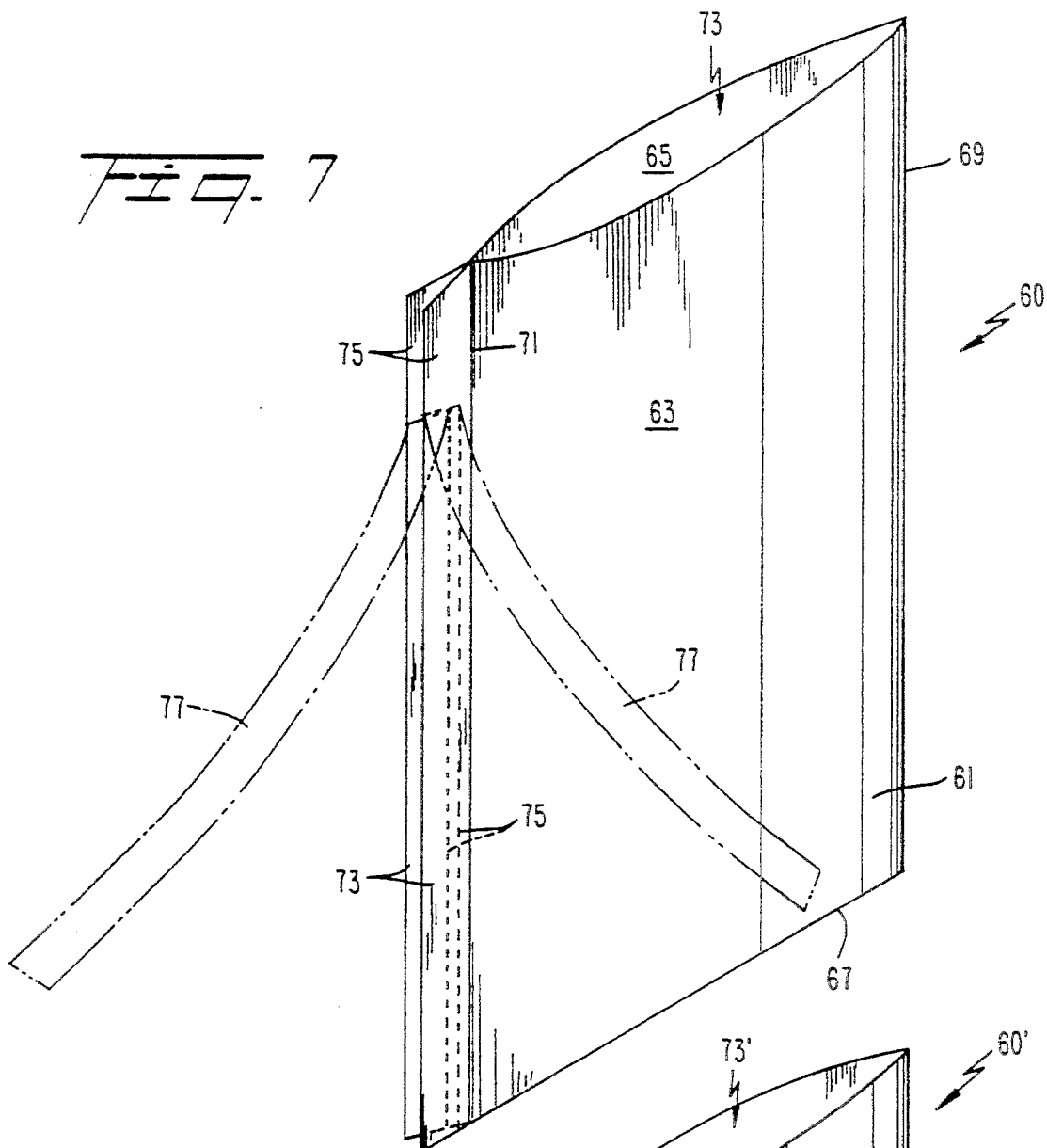

ENCLOSURE WITH INTEGRAL TIE MEMBER

CROSS-REFERENCE TO RELATED APPLICATIONS

This is a continuation-in-part application of U.S. patent application Ser. No. 07/891,121 filed Jun. 1, 1992, now U.S. Pat. No. 5,342,286.

FIELD OF THE INVENTION

This invention relates to an enclosure having a tie member integrally formed therewith for sealing an opening in the enclosure or securing the opening around an extremity or the like inserted therein. In particular, the enclosure can be a disposable sack-like member for enclosing and maintaining sterility of a bandaged or cast extremity or as a container for waste products or other articles.

BACKGROUND OF THE INVENTION

As is well known, a cast or bandage on an extremity for a lengthy period of time can be a source of great discomfort. Due to the necessity of keeping the cast or bandage dry, bathing, showering, or the like can be difficult. Furthermore, if a water impervious covering is used, it must be highly efficient because if water penetrates, for example, around the opening of a cast, patient discomfort will result in the form of itching, infection, or the like.

It is known to provide a sack-like member constructed of plastic sheeting material such as polyethylene for use in covering such extremity bandages. Such a device is shown in U.S. Pat. No. 4,727,864 wherein a sack-like member is intended to receive the extremity and a tie member is attached at one end thereof to the upper portion. The exposed portion of the tie member, as well as a spot on the sack edge, are coated with an adhesive. It is intended, then, that the tie member encircle the extremity so that the adhesive will seal the interface between the covering opening and the patient's skin against the penetration of water. This device is relatively expensive to manufacture in that a separate tie member must be welded at one end thereof to the opening of the container, and the adhesive applied both within the opening of the container at a spot, and along the length of the exposed portion of the tie.

It is also well known to provide tie members with food storage or garbage sacks which are of plastic material. For example, in U.S. Pat. No. 2,849,171, a tie member separate from the sack is provided on the upper portion thereof extending from side to side and the tie member is welded at each end to the sack. A loop, then, is formed by folding the tie member in the center which is used to tie the sack shut after it has been filled. Clearly, this would not be universally adaptable to covering extremities in that the loop would have to be very long and two hands would be required to tie the loop. If the extremity is a leg, then one could, presumably, tie the device. However, if the extremity injured is an arm, it would not be possible to tie such a device with one hand. Similarly, U.S. Pat. No. 3,186,626 describes integral tie members which are torn from the opening at either side thereof of a food storage sack. The tie members, then, are tied in a standard knot to close the sack opening. This also would require two hands and, therefore, it would not be universally applicable to injured persons without regard to whether the injury is located on the arm or leg.

SUMMARY OF THE INVENTION

It has been discovered, however, that an effective and efficient covering member can be provided which can be easily secured with one hand. The covering of this invention is a plastic sack-like member having a front and a back either secured at the edges thereof, or formed from tubular material, and having a closed end and an open end. The open end of the cover of this invention includes an extended lip along one side thereof which lip has a laterally extending strip of adhesive covered with a protective covering. The lip further is perforated along a substantial length thereof so that when the perforation is ripped, a tie member will be formed which is integral with the covering and when the protective covering is removed from the adhesive, the tie member, and the integral portion of the sacking extending therefrom along the lip will have an exposed adhesive coating.

The method of using the device of this invention, then, includes extending the extremity into the sack-like portion whereby the adhesive on the tie will hold the sack-like member of this invention by adhering it to the extremity it is wrapped around. The remaining portion of the opening may then be gathered around the extremity, and the tie member looped there around to adhesively seal the opening of the sack against the patient's skin.

In another embodiment, the lip can extend along a side edge of the sack-like member adjacent the sack-like member opening. In an alternative embodiment, a plurality of lips may be provided such that tie members formed therefrom can be knotted to seal the sack-like member around an extremity. Adhesive strips may also be used to further enhance securing the tie members in a given use.

In a further embodiment, the sack-like member may be used as an enclosure for containing, trash, waste or any desired object or objects. In this embodiment, the tie member or members are used to seal the sack-like opening by gathering portions of the front and back panels of the sack-like member together.

The sack-like member may also be manufactured and/or maintained in a sterile condition so as to provide a sterile environment within the sack-like member.

Accordingly, it is an object of this invention to provide a disposable water impervious covering material for extremities which can be universally applicable to both arms and legs in that a single tie member is provided which is integral to the sack and which is coated with adhesive so that it may be used to close the sack opening around the extremity and to be secured with a single hand.

It is yet another object of this invention to provide a method for maintaining a bandage or cast on an extremity in a dry condition while showering or bathing which includes the steps of providing a water impervious bag having an integral, single tie member formed on the open end, which comprises a perforation along the length of the lip which has the adhesive strip adhered thereto. The method includes partially separating the integral strip or tie from the bag, inserting the extremity into the bag, removing the protective backing from the adhesive strip, securing the unperforated portion to the extremity and winding the tie around the extremity to secure the opening of the bag thereto against the admittance of water.

Another object of the invention is to utilize the sack-like member as an enclosure for containing trash, waste material or other objects.

A further object of the invention is to provide a sterile sack-like member to minimize risk of infection or contamination when the sack-like member is used as a covering or a container.

BRIEF DESCRIPTION OF DRAWINGS

These and other objects will become readily apparent with reference to the drawings and following description wherein:

FIG. 1 is a perspective view of the covering of this invention.

FIG. 2 is a fragmentary front view showing the adhesive strip and tie member at the open end of the covering of FIG. 1.

FIG. 5 is a perspective view of a second embodiment of the invention.

FIG. 6 is a fragmentary perspective view of an alternative embodiment of the enclosure depicted in FIG. 5.

FIG. 7 a perspective view of another embodiment of the invention.

FIG. 8 is a fragmentary perspective view of an alternative embodiment of the enclosure depicted in FIG. 7.

DESCRIPTION OF THE INVENTION

Figure 3:
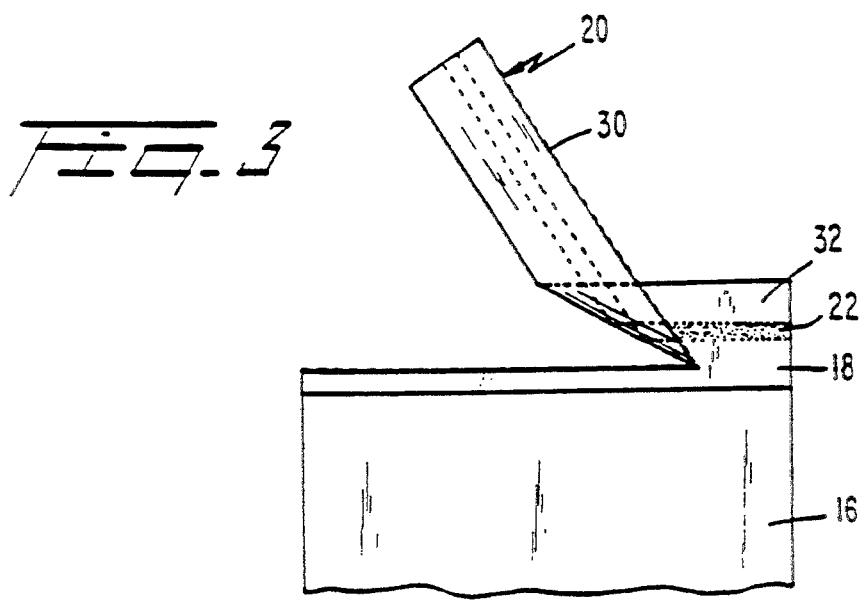
FIG. 3 is a view similar to FIG. 2 showing the integral tie member separated from the covering.

With attention to the drawings, the covering member of this invention 10 is preferably constructed of plastic sheeting material and configured as a sack having a closed bottom 12 and open top 14, a front panel 16 and a back panel 18. Back panel 18 defines an upstanding lip 20 intended to extend a substantial length beyond the opening 14 of the sack member 10.

The lip 20 integral with the back panel 18 mounts a longitudinally extending adhesive strip 22 extending the entire width thereof and spaced above the opening 18. The adhesive strip 22 is normally covered with a protective, separable covering strip 24 to preserve the tackiness of the adhesive strip 22. As is well known to those skilled in the art, protective strip 24 may be a coated paper, or the like, and is intended to be readily separable from the underlying adhesive strip 22 by hand.

The lip 20, integral with the back 18, also has a perforation 26 which extends from one side substantially across the lateral extent of the lip 20, preferably about four-fifths thereof, as shown in FIGS. 2 and 3. The lip 20 forms a tie member when the perforation is used to separate that portion thereof from the back panel 18 as by tearing by hand. See FIG. 3. When the perforation is torn, as shown in FIG. 3, a tie member 30 is formed and an integral securing portion 32 also formed from lip 20, as will be subsequently explained. The tie member 30 has the adhesive strip 22 extending the length thereof, and the integral securing portion 32 also has the adhesive strip 22 extending therealong.

In order to utilize the device of this invention, the covering 10 is used to cover that portion of the extremity which is bandaged or has a cast thereon. In order to do so, the hand or foot is inserted through the opening 14 into the sack member 10. The perforation 26 is then torn forming the integral tie member 30 and the adhesive strip covering 24 is removed, exposing the tacky adhesive strip 22 therealong.

Figure 4:
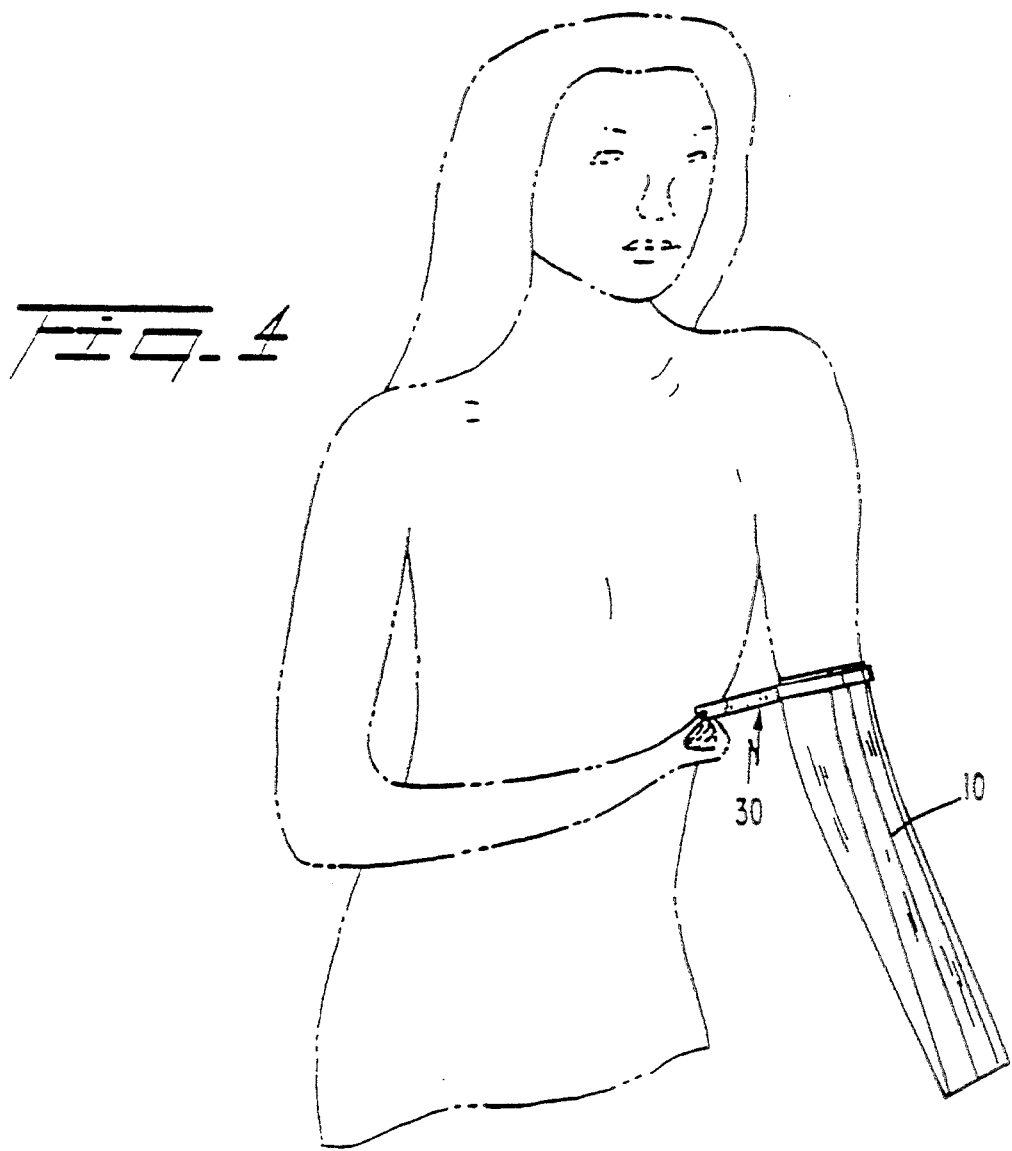
FIG. 4 is a representation of the covering member mounted on an arm with the tie member positioned to secure the covering of this invention to the arm.

The adhesive on securing segment 32 is then used to secure the sack member 10 to an adjacent portion of the extremity. With reference to FIG. 4, the securing portion 32 would be hidden behind the arm but affixed to the arm. The tie member 30 is then used to gather the opening 14 around the extremity and secure the same by passing the tie member 30 around the extremity and the covering member opening 14. In this way, the tie member 30 can be used to draw the periphery of the opening into gathers around the extremity and then pass therearound so that the adhesive member firmly secures the opening 18 around the extremity against water or the like.

When the device is removed, it is merely necessary to separate the adhesive on the securing portion 32 from the skin surface of the extremity and loosen the tie member 30 so that the entire covering 10 can be removed.

As will be apparent to those skilled in the art, whether the extremity to be covered is an arm or a leg, the device of this invention can be secured with one hand. In order to do so, it is necessary that the securing portion 32 and its adhesive strip secure the covering 10 against the skin so that as the periphery of opening 18 is gathered, the covering will not slip downwardly or laterally. The adhesive on the tie member 30, then, merely secures the gathers of the periphery of opening 18 to the extremity itself as it is tightened by pulling against the previously secured portion 32.

With reference now to FIG. 5, another embodiment of the invention is generally designated by the reference numeral 40 and is seen to include a sack-like member 41 having a front panel 43 and rear panel 45. The sack-like member 41 also includes a closed bottom 47, closed opposing side edges 49 and 51 and opening 53.

Extending outwardly from the side edge 51 is a lip 55 extending substantially the entire length of the side edge 51 and integrally attached thereto. It should be understood that the lip 55 is similar in nature to the lip 20 disclosed in FIG. 1. That is, the lip includes a perforated portion 57 terminating at reference numeral 59, thereby leaving a lip portion 52 integrally fastened to the side edge 51.

The lip 55 also includes an adhesive strip (not shown) covered by a covering strip 58. The adhesive and adhesive covering strip function in the same manner as described above for the covering depicted in FIG. 1. That is, the covering 58 is separated from the adhesive strip thereby exposing the adhesive strip for attachment purposes. In this manner, the lip 55, transformed into a tie member, can be used to secure the sack-like member around an extremity or to seal the sack opening for container use using the adhesive strip. The extent of the adhesive along the lip member is also variable depending on the particular size of the sack-like member 41 and the application. For example, the adhesive may extend along the entire length of the lip 55, the portion thereof forming the tie member or just near the free end of the tie member.

FIG. 6 depicts an alternative embodiment to the enclosure depicted in FIG. 5. In this embodiment, an enclosure is designated as reference numeral 40' including an opening 53' which extends between the entire width of the front panel 43'. In contrast to the FIG. 5 embodiment, the lip 55' extends outwardly from the side edge 51' and is integrally attached to the edge 54. The front panel 43' and back panel 45' are joined at the edge 54 as well as the adjacent edge 56. In this configuration, the lip 55' when separated from the side edge 51' forms a tie member integrally attached to the enclosure at the edge 54.

Still with reference to FIG. 6, this embodiment may be manufactured by modifying an enclosure having an opening 53' by first forming the closed side edge 51' and edge 54 followed by forming the perforated portion 57. In this mode, and since two lips 55' would be formed from portions of the front and back panel of the enclosure, one lip can be removed so as to leave the other lip in place for separation to form the tie member.

With reference now to FIG. 7, a third embodiment of the present invention is generally designated by the reference numeral 60 and is seen to include a sack-like member 61 having a front panel 63 and rear panel 65. The sack-like member 61 includes a bottom edge 67, opposing side edges 69 and 71 and opening 73.

In this embodiment, a pair of lips 73 are provided extending outwardly from the side edge 71. Again, these lips are configured in a similar manner as the lip 55 in the embodiment depicted in FIG. 5. That is, each lip includes a perforated portion 75 which permits the lip 73 to be separated from the side edge 71, thereby forming a pair of tie members. Each separated tie member is integrally attached to the sack-like member 61 via the portions 75 which remain attached at the side edge 71.

The lips 73 are shown in phantom as tie members 77 to better illustrate the separation via the perforated portion 75.

In this embodiment, the tie members 77 can be utilized to secure the opening 73 around an extremity or, alternatively, to seal the opening 73 to use the sack-like member as an enclosure or container. Using the sack-like member as a container, the disposability aspect of the sack-like member facilitates the use as a trash or waste container for disposal purposes.

To facilitate securing the tie members 77, adhesive and a removable covering may be applied thereto similar to adhesive 22 and cover 24 shown in FIG. 2.

This embodiment is particularly adapted for covering lower extremities of a person since the pair of tie members 77 may require two hands for fastening. Alternatively, the tie members 77 may be utilized to seal the opening 73 so as to use the sack-like member as an enclosure or container for waste, trash or other objects as described above.

FIG. 8 depicts an alternative embodiment of the sack-like member 61 similar to the alternative embodiment depicted in FIG. 6. That is, the sack-like member 61' has an opening 73' which extends along the entire width of the sack-like member 61'.

As described above for the enclosure 40', the tie members 77' terminate at the sealed edge 79 to form the integral attachment with the sack-like member 61'. The front panel 63' and the back panel 65' join to form the side edge 81 as well as the edge 79. As described above, this embodiment may be formed by modifying an enclosure having an opening 73' by first subsequently sealing the front and back panels together to form the edge 79 and 71'. Following this step, the original edge of the enclosure corresponding to the edge 81 is slit and the perforated portion 75' are formed as the lips. Separation of the lips along the perforations 75' results in formation of the tie members 77'.

It is intended that the device of this invention be constructed of light-weight plastic material which is water impervious. The adhesive strip is also intended to be formed of an adhesive compatible with human skin or the material of the enclosure and the dimensions of the device of this invention may be changed, depending upon whether it is intended to cover an entire extremity, an arm or a leg, or merely a hand or a foot or be used as a container or receptacle. The sack member may be formed of tubular material and welded to form the closed bottom or it may be formed of sheeting material folded to form one longitudinal edge and welded to form the closed bottom and opposite longitudinal edge. The construction of the device will be obvious to those skilled in the art. While it is preferred to construct the device of this invention of polyethylene sheeting material, the invention is not intended to be limited to the particular materials of construction or the process used for forming the sack-like member. The perforation which separates the lip from the sack like member to form the tie members disclosed and the securing portion preferably extends about four-fifths of the width of the sack or covering or the length of the sack member. However, this invention is not intended to be limited to a particular length of the perforation for any of the disclosed embodiments.

The light-weight plastic material of the invention may also be packaged and/or manufactured in a sterile fashion using conventional techniques to further enhance the use of the sack member for covering extremities or maintaining objects in a sterile condition. By maintaining sterility of the plastic material, the risk of contamination or infection of a bandaged or cast extremity is reduced. Moreover, the sterility of the sack member also facilitates maintaining an object or objects in a sterile condition when the sack member is used as a container or receptacle, particularly for use in the medical field.

The invention may be embodied in other specified forms without departing from the spirit or essential characteristics thereto. The present embodiments are therefore to be considered in all respects as illustrative and not restrictive, the scope of the invention being indicated by the appended claims rather than by the foregoing description, and all changes which may come within the meaning and range of equivalency of the claims are therefore intended to be embrace therein.

We claim:

1. An enclosure comprising:
   a sack-like member of water impervious material having a front panel and a back panel, said front and back panels interconnected to form a closed bottom, an open top and opposing edges, said front and back panels being upstanding to define said open top; said back panel including a lip as an integral part thereof, said lip extending upwardly from and beyond the open top such that free opposing ends of said lip are aligned with respective said opposing edges of said sack-like member so that said lip is between said opposing edges; an adhesive strip extending laterally across the length of said lip; removable means covering said strip for protecting said adhesive and
   a perforation line formed in said lip and having a length less than the length of said lip to form an integral tie member having a free end as one of said free opposing ends of said lip and a securing tie member segment integral with said tie member and said back panel, said adhesive strip extending the length of said tie member and securing segment;

wherein said tie member can seal said open top by gathering portions of said front and said back panel adjacent said open top to form a container.

2. The enclosure of claim 1 wherein said adhesive strip extends laterally across said lip parallel to the open top of said sack member.

3. The enclosure of claim 2 wherein said lip has an upper edge extending the length thereof parallel to the open top of said sack-like member and said adhesive strip is disposed between the open top and upper edge.

4. The enclosure of claim 2 wherein said perforation line is disposed between said adhesive strip and the open top of said sack-like member.

5. The covering of claim 1 wherein said tie member is about four times longer than said securing segment.

6. The covering of claim 1 wherein said perforation line extends about four-fifths of the length of said lip.

7. A waste material enclosure comprising:

a sack-like member of water impervious material having a front panel and a back panel, said front and back panel interconnected to form a closed bottom, an open top and opposing edges, said front and back panels being upstanding to define said open top for receiving said waste material; said back panel including a lip as an integral part thereof, said lip extending upwardly from and beyond the open top such that free opposing ends of said lip are aligned with respective said opposing edges of said sack-like member so that said lip is between said opposing edges; an adhesive strip extending laterally across the length of said lip; removable means covering said strip for protecting said adhesive; and a perforation line formed in said lip and having a length less than the length of said lip to form an integral tie member having a free end as one of said free opposing ends of said lip and a securing tie member segment integral with said tie member and said back panel, said adhesive strip extending the length of said tie member and securing segment;

wherein said tie member can seal said open top by gathering portions of said front and said back panel adjacent said open top to form said waste material enclosure.

8. The waste material enclosure of claim 7 wherein said adhesive strip extends laterally across said lip parallel to the open top of said sack member.

9. The waste material enclosure of claim 7 wherein said lip has an upper edge extending the length thereof parallel to the open top of said sack-like member and said adhesive strip is disposed between the open top and upper edge.

10. The waste material enclosure of claim 7 wherein said perforation line is disposed between said adhesive strip and the open top of said sack-like member.

11. The waste material enclosure of claim 7 wherein said tie member is about four times longer than said securing segment.

12. The waste material enclosure of claim 7 wherein said perforation extends about four-fifths of the length of said lip.

* * * * *